United States Patent [19]

Sauer

[11] 4,417,051
[45] Nov. 22, 1983

[54] PROCESS FOR THE PREPARATION OF 8α-SUBSTITUTED 6-METHYLERGOLINES

[75] Inventor: Gerhard Sauer, Berlin, Fed. Rep. of Germany

[73] Assignee: Schering, Aktiengesellschaft, Berlin and Bergkamen, Fed. Rep. of Germany

[21] Appl. No.: 262,872

[22] Filed: May 12, 1981

[51] Int. Cl.³ .................... C07D 519/02
[52] U.S. Cl. .................... 546/67; 546/68; 546/69
[58] Field of Search .................... 546/67, 68, 69

[56] References Cited

U.S. PATENT DOCUMENTS 3,901,893 8/1975 Karacsony et al. .................... 546/69
3,968,111 7/1976 Bach et al. .................... 260/285.5
4,075,212 2/1978 Bach et al. .................... 260/285.5

FOREIGN PATENT DOCUMENTS 477447 10/1969 Switzerland .................... 546/69
1048555 11/1966 United Kingdom .................... 546/67
1199233 7/1970 United Kingdom .................... 546/67

OTHER PUBLICATIONS

Medicinal Chemistry, Burger, 3rd Edition, Part II, Wiley Interscience (1970) p. 1514.
V. Zikan and M. Semonsky, Pharmazie, 23 (1968) pp. 147, 148.
A. Hoffman, Die Mutterkornalkaloide, Enke Verlag, Stuttgart 1964, pp. 38–50.

Primary Examiner—Nicholas S. Rizzo
Assistant Examiner—G. Hendricks
Attorney, Agent, or Firm—Millen & White

[57] ABSTRACT

A process for preparing an 8α-substituted 6-methyl-10α-H-ergoline of the formula

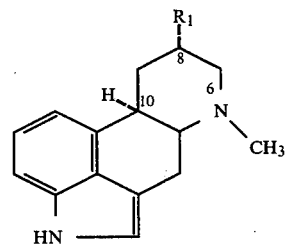

wherein $R_1$ is $HN-CO-NX_2$ (wherein X is hydrogen, methyl or ethyl), $CO-NH-NX_2$, $CO-NX_2$, or $CH_2OX$, comprises reducing the corresponding 8α-substituted-9,10-didehydro-6-methylergoline, with an alkali metal or alkaline earth metal dissolved in a nitrogen compound which is a primary or secondary $C_{1-3}$-alkylamine, a hexa-$C_{1-2}$-alkyl-phosphoric triamide or ammonia at a temperature of $-70°$ to $-30°$ C.

14 Claims, No Drawings

PROCESS FOR THE PREPARATION OF 8α-SUBSTITUTED 6-METHYLERGOLINES

BACKGROUND OF THE INVENTION

The present invention concerns a process for preparing 8α-substituted 6α-methyl-10α-H-ergolines. Such compounds are either themselves biologically active, e.g., as inhibitors of endogen prolactin secretion and, therefore, as suppressants for nidation, in mammals, e.g., 3-(6-methyl-8α-ergolinyl)-1,1-diethylurea, or are intermediates for the production of other compounds which are biologically active, e.g., dironyl, sulergine and delergotrile having the above mentioned biological activity.

It is known that the trans-linked 10α-H-ergolines can be readily obtained from 8β-substituted didehydroergolines by the catalytic hydrogenation of the 9,10-double bond. The situation, however, is different in the case of the 8α-substituted 9,10-didehydroergolines. Catalytic hydrogenation of 8α-substituted 9,10-didehydroergolines always results in mixtures consisting of the trans-linked 10α-H-ergolines and the cis-linked 10β-H-ergolines. However, biologically active compounds are derived solely from the trans-linked ergolines, such as, for example, the conventional ergolines, dironyl, sulergine, and delergotrile.

Thus, in the catalytic hydrogenation of lisuride to dironyl with Raney nickel, depending upon the nature of the catalyst and the solvent, maximum yields of 66% of desired product are obtained (DOS [German Unexamined Laid-Open Application] No. 2,238,540), wherein the ratio of the desired 10α-H-isomer to the undesired 10β-H-isomer is about 4:1.

SUMMARY OF THE INVENTION

Accordingly, it is an object of the present invention to provide a method, by means of which 8α-substituted 9,10-didehydroergolines can be selectively reduced to the corresponding 10α-H-ergolines.

Upon further study of the specification and appended claims, further objects and advantages of this invention will become apparent to those skilled in the art.

These objects have been attained by providing a process for reducing 8α-substituted 9,10-didehydroergolines to the desired 10α-H-ergolines in a high yield using alkali metals or alkaline earth metals in nitrogen compounds, at temperatures of −30° to −70° C., essentially without the occurrence of mixtures of 10α-H- and 10β-H-isomers.

DETAILED DISCUSSION

The results of the reaction of this invention is surprising insofar as a person skilled in the art would have expected a mixture of 10α-H- and 10β-H-isomers, in analogy to the results of other hydrogenation processes.

Preferred 8α-substituted-6-methyl-10α-H-ergolines preparable by the process of this invention are of the formula

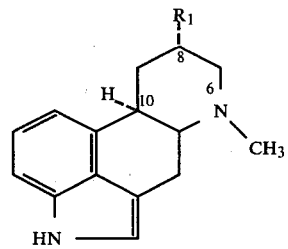

wherein $R_1$ is $-NH-CO-NX_2$ (X being H, methyl or ethyl), $-CO-NH-NX_2$, $-CO-NX_2$ or $-CH_2OX$. The starting material 8α-substituted-9,10-didehydro-6-methylergolines used to prepare such compounds per this invention are all known. See, e.g., V. Zikan and M. Semonsky, Pharmazie, 23(1968) 147; A. Hofmann, Die Mutterkornalkaloide, Enke-Verlag, Stuttgart 1964.

The amount of alkali metal or alkaline earth metal used to reduce such compounds is generally 2–100, especially 5–20 molar equivalents related to starting compound. The amount of nitrogen compound is generally 0.01–0.5 ml per mg of metal so employed.

By "nitrogen compound" is meant an N-containing compound which dissolves the mentioned metal such as ammonia, a primary and secondary $C_{1-3}$-alkylamine, e.g., methylamine and dimethylamine, a hexa-$C_{1-2}$-alkylphosphoric triamide, e.g., hexamethylphosphoric triamide and hexaethylphosphoric triamide.

The process of this invention is suitably conducted by dissolving the alkali metal or alkaline earth metal, such as lithium, sodium, potassium, or calcium, in the nitrogen compound such as ammonia, at a temperature below −30° C. Subsequently, the starting material to be hydrogenated is added. In this connection, it is advantageous to include a solubilizer, i.e., an inert solvent, generally in an amount of 1–1000 ml per mmole of starting compound. Suitable solvents include, for example, aliphatic ethers, such as diethyl ether, methylethyl ether, dimethoxyethane, and cyclic ethers, such as tetrahydrofuran, and dioxane, as well as, N-methylpyrrolidone, dimethylformamide, dimethylacetamide, and tetramethyl urea.

It has been found that the addition of an arylamine to the reaction mixture is especially advantageous. Suitable arylamines for use in the present invention include phenyl- and substituted phenyl-amines and -hydrazines, for example, aniline, methylaniline, anisidine, o-dianisidine, diphenylamine, ethylaniline, p-phenylenediamine, dimethoxyaniline, phenylhydrazine, dinitrophenylhydrazine, and benzidine. The arylamine is generally added to the reaction mixture in an amount of 0.5–5, preferably 1–2 molar equivalents based on the number of equivalents of starting material ergoline employed.

The reaction generally requires about 20–200 minutes for completion and, in most cases, is entirely consummated after 30–40 minutes. Yield generally are 70–95 molar %; the minor amount of 10β-H isomer found being only 1–10 molar % in general.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

At $-70°$ C., 100 mg of lithium is dissolved in about 10 ml of anhydrous ammonia; at this temperature, 1 millimole of 3-(9,10-didehydro-6-methyl-8α-ergolinyl)-1,1-diethylurea I and 1.5 mmol of aniline in 5 ml of tetrahydrofuran are added within a few minutes. If the solution becomes decolorized, a small amount of lithium is additionally introduced. Then, the mixture is stirred for 30 minutes at $-70°$ C., combined with ammonium chloride until decolorizing occurs, and the ammonia is removed by evaporation. The residue is taken up in saturated sodium bicarbonate solution, saturated with sodium chloride, and extracted with chloroform or ethyl acetate. The organic phase is dried with sodium sulfate, evaporated, and the residue is crystallized from ethanol, thus obtaining 3-(6-methyl-8α-ergolinyl)-1,1-diethylurea II in an 85% yield.

$[\alpha]_D = +29°$.

EXAMPLE 2

Analogously to Example 1, 6-methylergoline-8α-carboxylic acid amide IV is obtained from isolysergic acid amide III; 6-methylergoline-8α-carboxylic acid diethylamide VI is obtained from isolysergic acid diethylamide V; 6-methylergoline-8α-carboxylic acid hydrazide VIII is produced from isolysergic acid hydrazide VII; and 6-methylergoline-8α-methanol X is obtained from isolysergol IX.

The following experiments were conducted:

| Starting Material | Metal | Arylamine | Final Product | Yield (%) | $[\alpha]_D°$ |
|---|---|---|---|---|---|
| I | Li | — | II | 70 | +30 |
| I | Li | Aniline | II | 85 | +29 |
| I | Li | Methylaniline | II | 72 | +29 |
| I | K | Aniline | II | 75 | +29 |
| I | Li | Anisidine | II | 94 | +30 |
| I | Li | o-Dianisidine | II | 90 | +29 |
| I | Li | Diphenylamine | II | 75 | +29 |
| I | Li | p-Phenylenediamine | II | 71 | +30 |
| III | Li | Aniline | IV | 92 | +2 |
| III | Na | Aniline | IV | 81 | +1 |
| V | Li | Aniline | VI | 78 | −67 |
| VII | Li | — | VIII | 69 | −23 |
| VII | Li | Aniline | VIII | 87 | −24 |
| IX | Li | Aniline | X | 86 | −70 |
| I | Li | 3,5-Dimethoxyaniline | II | 73 | +30 |
| I | Li | Benzidine | II | 77 | +30 |
| I | Li | Phenylhydrazine | II | 90 | +30 |
| I | Li | 2,4-Dinitrophenyl-hydrazine | II | 71 | +30 |

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing an 8α-substituted 6-methyl-10α-H-ergoline of the formula

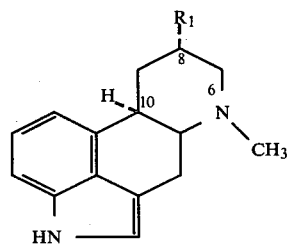

wherein $R_1$ is NH—CO—NX$_2$ (wherein X is hydrogen, methyl or ethyl), CO—NH—NX$_2$, CO—NX$_2$, or CH$_2$OX, comprising reducing the corresponding isolysergic compound, 8α-substituted-9,10-didehydro-6-methylergoline, with an alkali metal or alkaline earth metal dissolved in a nitrogen compound which is a C$_{1-3}$-alkylamine, a hexa-C$_{1-2}$-alkyl-phosphoric triamide or ammonia at a temperature of $-70°$ to $-30°$ C., thereby obtaining essentially only the 8α-substituted, 10α-H compound.

2. A process of claim 1 wherein the nitrogen compound is ammonia, methylamine or hexamethylphosphoric triamide.

3. A process of claim 1 wherein the reaction is conducted in the presence of an inert solvent for the ergolines.

4. A process of claim 3, wherein the solvent is an ether.

5. A process of claim 1, wherein the reaction is conducted in the presence of an arylamine which is a phenyl- or substituted phenyl-amine or -hydrazine.

6. A process of claim 5, wherein the arylamine is aniline, anisidine or phenylhydrazine.

7. A process of claim 2, wherein ammonia is the nitrogen compound.

8. A process of claim 1, wherein the alkali metal or alkaline earth metal is lithium.

9. A process of claim 1 wherein $R_1$ is NH—CO—NX$_2$.

10. A process of claim 1 wherein $R_1$ is CO—NH—NX$_2$.

11. A process of claim 1 wherein $R_1$ is CO—NX$_2$.

12. A process of claim 1 wherein $R_1$ is CH$_2$OX.

13. A process of claim 1 wherein the reduction is carried out using an alkali metal.

14. A process of claim 1 wherein the reduction is carried out using an alkaline earth metal.

* * * * *